(12) United States Patent
Zhang et al.

(10) Patent No.: US 11,564,822 B2
(45) Date of Patent: Jan. 31, 2023

(54) STOMACH LINING PATCH WITH CENTRAL FIXATION

(71) Applicant: W. L. Gore & Associates, Inc., Newark, DE (US)

(72) Inventors: Ji Zhang, Newark, DE (US); Sherif A. Eskaros, Elkton, MD (US); Nathan K. Mooney, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 397 days.

(21) Appl. No.: 16/629,131

(22) PCT Filed: Jul. 7, 2017

(86) PCT No.: PCT/US2017/041066
§ 371 (c)(1),
(2) Date: Jan. 7, 2020

(87) PCT Pub. No.: WO2019/009917
PCT Pub. Date: Jan. 10, 2019

(65) Prior Publication Data
US 2020/0289302 A1    Sep. 17, 2020

(51) Int. Cl.
*A61F 5/00*    (2006.01)

(52) U.S. Cl.
CPC .......... *A61F 5/0076* (2013.01); *A61F 5/0089* (2013.01)

(58) Field of Classification Search
CPC ..... A61F 5/0076; A61F 5/0089; A61F 5/0069
See application file for complete search history.

(56) References Cited

U.S. PATENT DOCUMENTS

| 8,628,554 B2 | 1/2014 | Sharma |
| 2003/0120292 A1 | 6/2003 | Park et al. |
| 2003/0176884 A1 | 9/2003 | Berrada et al. |
| 2004/0092892 A1 | 5/2004 | Kagan et al. |
| 2008/0255594 A1 | 10/2008 | Cully |
| 2008/0255678 A1 | 10/2008 | Cully et al. |

(Continued)

FOREIGN PATENT DOCUMENTS

| CN | 101500517 A | 8/2009 |
| CN | 102917666 A | 2/2013 |

(Continued)

OTHER PUBLICATIONS

British Journal of Hospital Medicine vol. 77, No. 3Supplement on Abdominal SurgeryFree Access Which mesh or graft? Prosthetic devices for abdominal wall reconstruction (Year: 2016).*
International Preliminary Report on Patentability received for PCT Patent Application No. PCT/US2017/041066, dated Jan. 16, 2020, 9 pages.

(Continued)

*Primary Examiner* — Brian A Dukert

(57) ABSTRACT

A stomach lining patch includes a collapsible frame, a membrane covering the collapsible frame, collapsible frame and the membrane providing a collapsed configuration suitable for endoluminal delivery to a stomach of a patient and an expanded configuration suitable for lining an internal surface of a gastric wall of the stomach, and a set of anchoring arms extending from the collapsible frame and being configured to pass through a puncture in the gastric wall and lay flat against an outer surface of the gastric wall when the collapsible frame and the membrane are in an expanded configuration lining the internal surface of the gastric wall.

13 Claims, 5 Drawing Sheets

(56) References Cited

U.S. PATENT DOCUMENTS

| | | |
|---|---|---|
| 2009/0222032 A1 | 9/2009 | Horndeski |
| 2009/0259246 A1 | 10/2009 | Eskaros |
| 2010/0114128 A1 | 5/2010 | Coleman et al. |
| 2013/0197562 A1* | 8/2013 | Burnes ............... A61F 5/0013 606/191 |
| 2014/0236064 A1 | 8/2014 | Binmoeller et al. |
| 2014/0350658 A1 | 11/2014 | Benary et al. |
| 2015/0005810 A1 | 1/2015 | Center et al. |
| 2015/0313595 A1 | 11/2015 | Houghton |
| 2015/0313596 A1 | 11/2015 | Todd |
| 2015/0313597 A1 | 11/2015 | Sambandam |
| 2015/0313598 A1 | 11/2015 | Todd |
| 2015/0313599 A1* | 11/2015 | Johnson ............... A61B 17/11 606/191 |
| 2016/0106565 A1* | 4/2016 | Sharvit ............... A61F 2/04 604/8 |
| 2016/0174987 A1 | 6/2016 | Dalle et al. |

FOREIGN PATENT DOCUMENTS

| | | |
|---|---|---|
| JP | 2012-507376 A | 3/2012 |
| JP | 2016-507333 A | 3/2016 |
| JP | 2016-526438 A | 9/2016 |
| KR | 10-2013-0110413 A | 10/2013 |
| WO | 88/00027 A1 | 1/1988 |
| WO | 2010/051909 A1 | 5/2010 |
| WO | 2014/130850 A1 | 8/2014 |
| WO | 2015/044422 A1 | 4/2015 |

OTHER PUBLICATIONS

International Search Report and Written Opinion received for PCT Patent Application No. PCT/US2017/041066, dated Apr. 9, 2018, 13 pages.

International Search Report and Written Opinion received for PCT Patent Application No. PCT/US2017/041069, dated Mar. 15, 2018, 10 pages.

* cited by examiner

STOMACH LINING PATCH WITH CENTRAL FIXATION

CROSS-REFERENCE TO RELATED APPLICATION

This application is a U.S. 371 Application of International Application PCT/US2017/041066, filed Jul. 7, 2017, which is herein incorporated by reference in its entirety.

FIELD

The present disclosure relates to medical devices, and more particularly, but without limitation, to bariatric surgical therapies.

BACKGROUND

Millions of adults in the United States and elsewhere are obese. Many adults with obesity further suffer from Type 2 Diabetes Mellitus (T2DM) and/or with hypertension. Obesity related disorders, including diabetes, cost the United States and worldwide healthcare systems hundreds of billions of dollars annually.

Bariatric surgeries, such as vertical sleeve gastrectomy and Roux-en-Y gastric bypass, are effective treatments for both obesity and T2DM. Recent clinical studies demonstrated bariatric surgeries generally provide significantly more excess weight loss in obese patients as compared to lifestyle and medical therapies. Some studies have shown that more than half of bariatric surgery patients also achieve remission of diabetes within a year of surgery.

SUMMARY

This disclosure includes a stomach lining patch suitable for endoscopic delivery and implantation. The stomach lining patch is configured to cover an internal surface of a gastric wall of a patient to limit nutrient contact, which can lead to significant weight loss for a patient.

In one example, this disclosure is directed to a stomach lining patch comprising a collapsible frame, a membrane covering the collapsible frame, and a set of anchoring arms extending from the collapsible frame. The collapsible frame and the membrane have a collapsed configuration that is suitable for endoluminal delivery to a stomach of a patient and an expanded configuration that is suitable for lining an internal surface of a gastric wall of the stomach. The anchoring arms are configured to pass through a puncture in the gastric wall and lay flat against an outer surface of the gastric wall when the collapsible frame and the membrane are in the expanded configuration lining the internal surface of the gastric wall.

In another example, this disclosure is directed to an assembly comprising an endoscopic delivery catheter, and a stomach lining patch in a collapsed configuration within the endoscopic delivery catheter. The stomach lining patch includes a collapsible frame, a membrane covering the collapsible frame, and a set of anchoring arms extending from the collapsible frame. The collapsible frame and the membrane have a collapsed configuration that is suitable for endoluminal delivery to a stomach of a patient and an expanded configuration that is suitable for lining an internal surface of a gastric wall of the stomach. The anchoring arms are configured to pass through a puncture in the gastric wall and lay flat against an outer surface of the gastric wall when the collapsible frame and the membrane are in the expanded configuration lining the internal surface of the gastric wall.

In a further example, this disclosure is directed to a method of implanting a stomach lining patch within the stomach of a patient. The method includes inserting an endoscopic delivery catheter through an esophagus of the patient to locate a distal end of the endoscopic delivery catheter within a stomach of the patient, forming a puncture in a gastric wall of the stomach, and delivering the stomach lining patch in a collapsed configuration to the stomach via the endoscopic delivery catheter. The stomach lining patch includes a collapsible frame, a membrane covering the collapsible frame, collapsible frame, and a set of anchoring arms extending from the collapsible frame. The collapsible frame and the membrane have a collapsed configuration that is suitable for endoluminal delivery to a stomach of a patient and an expanded configuration that is suitable for lining an internal surface of a gastric wall of the stomach. The method further includes inserting the set of anchoring arms through the puncture the gastric wall and deploying the stomach lining patch from the distal end of the endoscopic delivery catheter to expand the stomach lining patch from the collapsed configuration to an expanded configuration. Once deployed, the set of anchoring arms lay flat against an outer surface of the gastric wall and the collapsible frame and the membrane line an internal surface of the gastric wall.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1A:
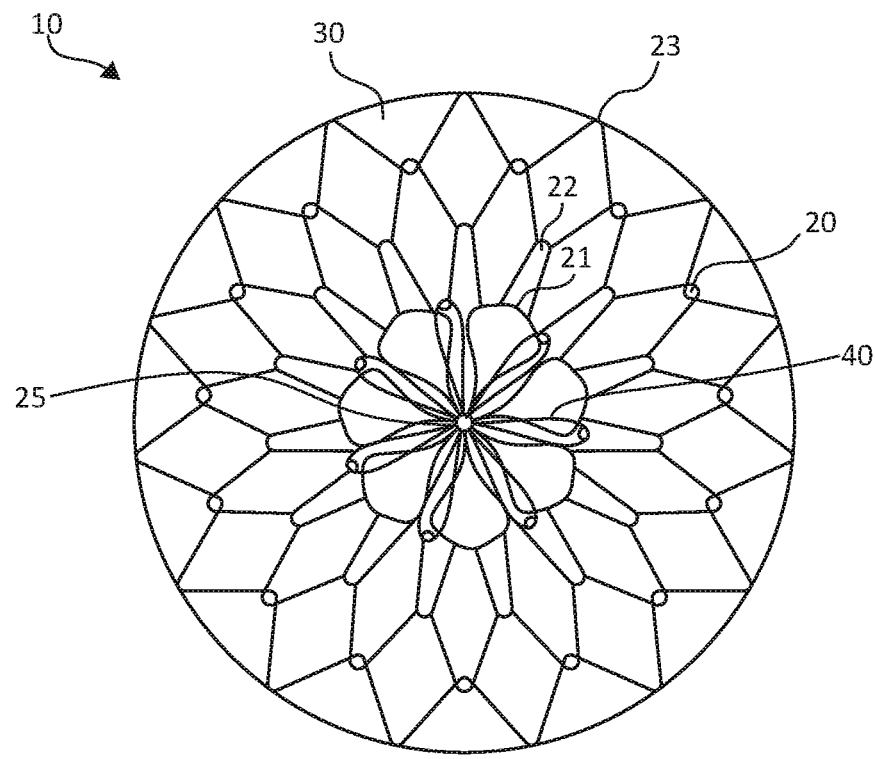
FIGS. 1A-1B illustrate a stomach lining patch with a central fixation, the stomach lining patch being suitable for endoscopic delivery and implantation within a patient.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Figure 1B:
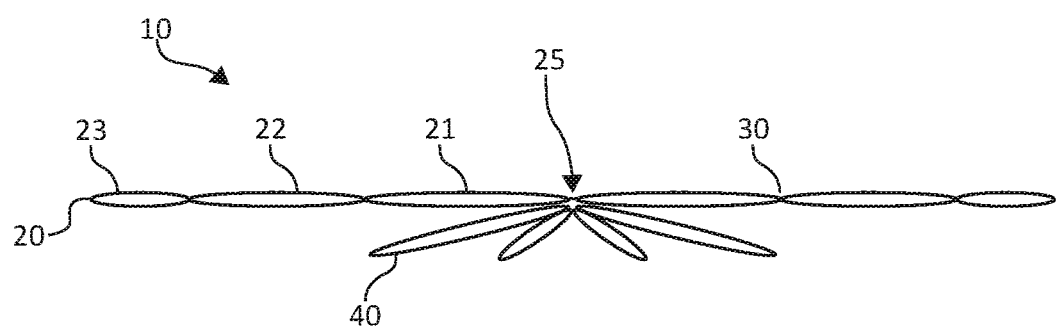

FIGS. 1A-1B illustrate a stomach lining patch 10, which is suitable for endoscopic delivery and implantation within a patient. More specifically, FIG. 1A illustrates a top view of the stomach lining patch 10, whereas FIG. 1B illustrates a side view of the stomach lining patch 10. The stomach lining patch 10 includes a collapsible frame 20, a membrane 30 covering the collapsible frame 20, and a set of anchoring arms 40 that provide central fixation for the stomach lining patch 10.

The collapsible frame 20 is formed from one or more elongated elements shaped to form a set of concentric interwoven or interconnected undulating rings, including a first undulating ring 21, a second undulating ring 22, and a third undulating ring 23, radiating from a center 25 of the collapsible frame 20. In different examples, the undulating rings may represent separate rings or include a single wire in arranged in a coil to form more than one, such as all, of rings 21, 22, 23. The first undulating ring 21 forms a series of petals surrounding the center 25. The second undulating ring 22 forms peaks and valleys with the valleys woven through or interconnected with the petals of the first undulating ring 21. The third undulating ring 23 forms peaks and valleys with the valleys woven through or interconnected with the peaks of the second undulating ring 22. For example, overlapped apices can be held in place with adhesive or the graft material.

Figure 2A:
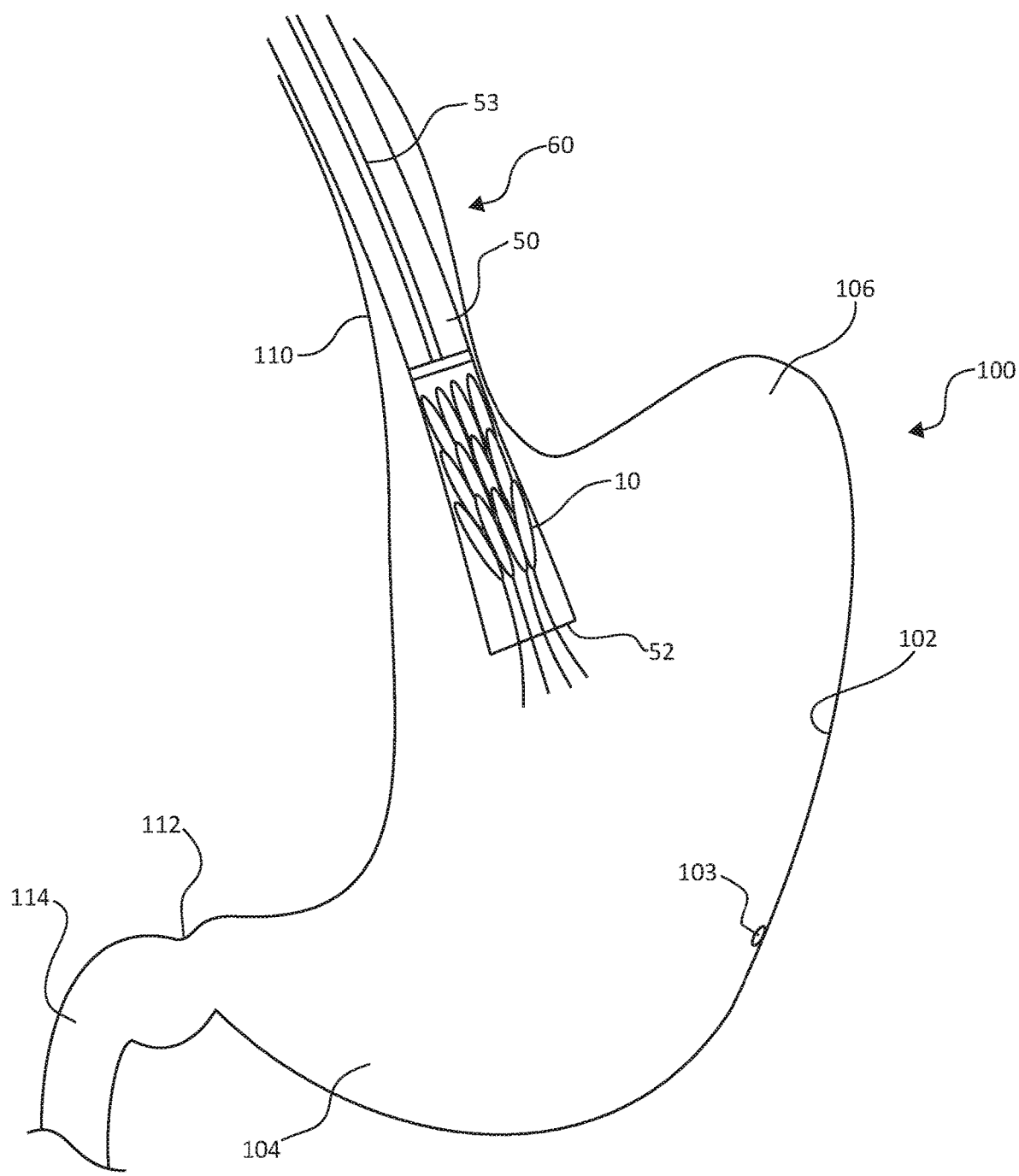
FIGS. 2A-2D are conceptual illustrations of an endoscopic implantation of the stomach lining patch of FIGS. 1A-1B.
Figure 2B:
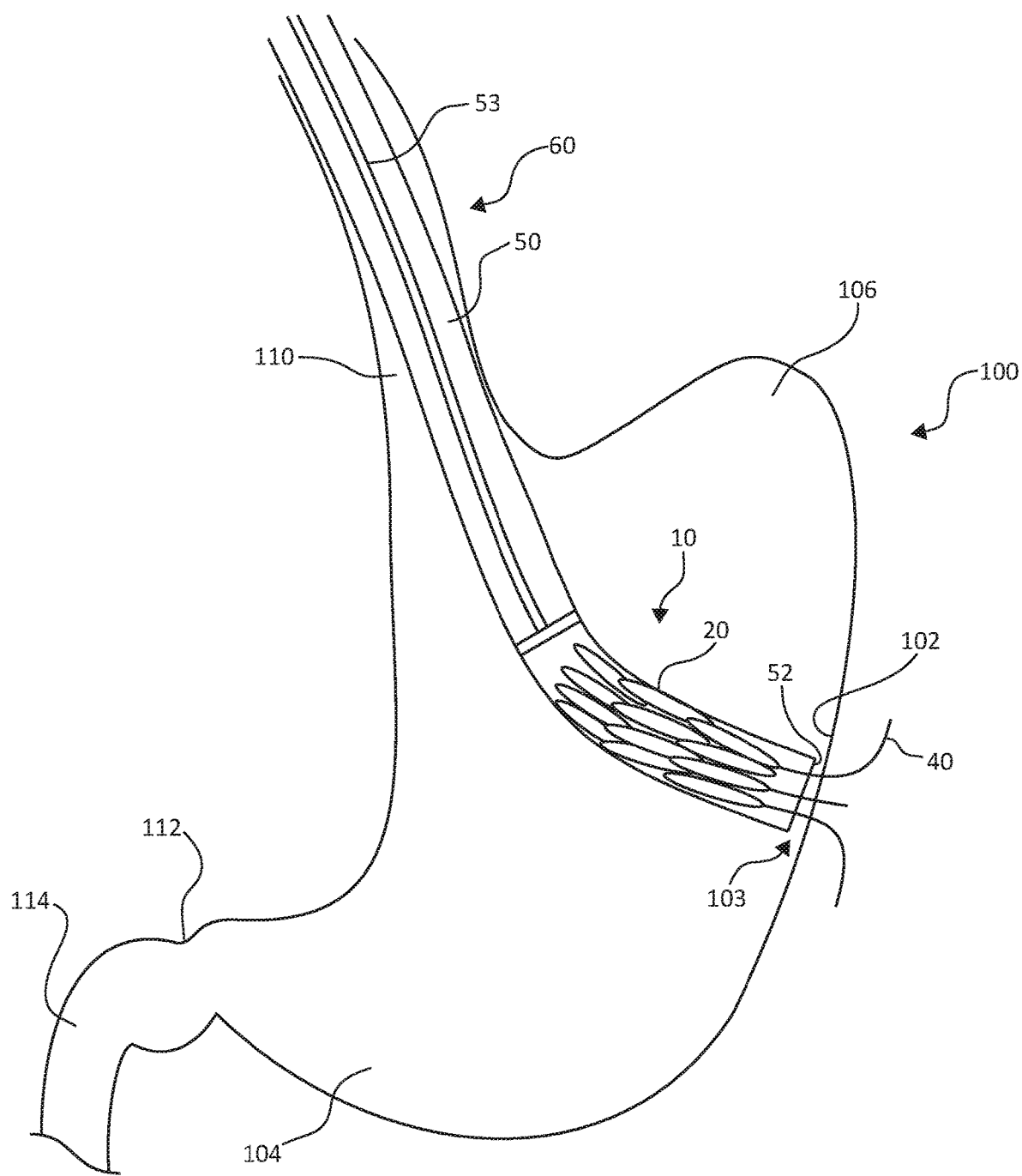
Figure 2C:
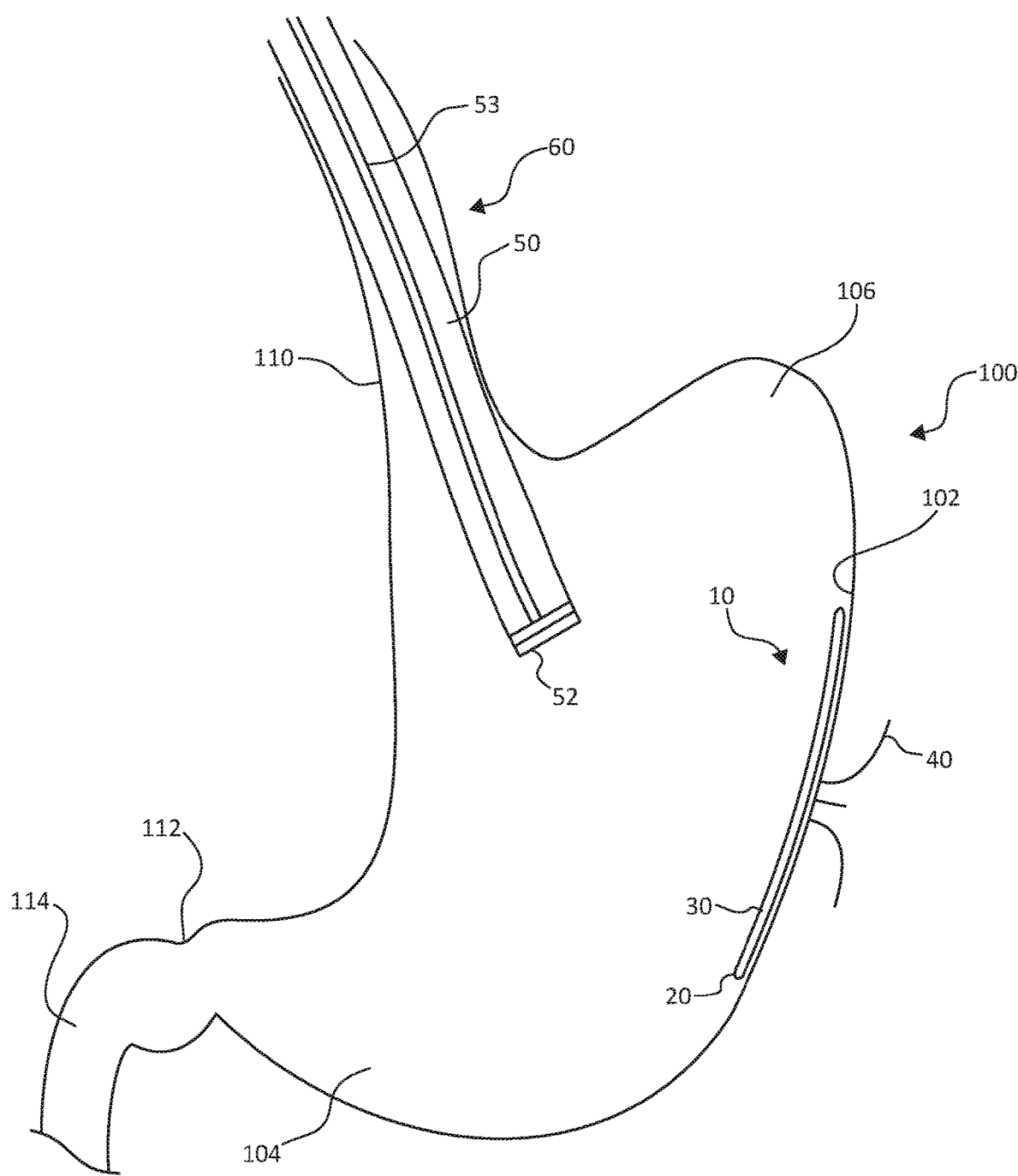

The concentric arrangement of the undulating rings 21, 22, 23 provides a collapsed configuration suitable for endoscopic delivery to a stomach of a patient, as shown in FIG. 2A, as well as an expanded configuration suitable for lining an internal surface of a gastric wall of a stomach, as shown in FIG. 2C. The collapsible frame 20, when in the expanded configuration, is compliant to remain in contact with the internal surface of the gastric wall during peristalsis, for example, or other movement of the stomach wall.

In some examples, the collapsible frame 20 may be formed from a metal material, such as a metal wire. In some examples, the collapsible frame 20 may be formed from a superelastic material, such as a nitinol wire. Such examples may allow a collapsed configuration suitable for endoscopic delivery through elastic deformation of the expanded configuration. Alternatively, the collapsible frame 20 may be formed from a cut tube, such as a nitinol tube. Such examples may provide interconnected connections between the undulating rings 21, 22, 23.

The collapsible frame 20 serves as a skeleton to support the membrane 30, and the membrane 30 covers the collapsible frame 20. The membrane 30 is suitable to limit nutrient contact when the stomach lining patch 10 is lined against an internal surface of a gastric wall of a stomach. In some examples, the membrane 30 may include or be formed entirely, or primarily (e.g., 80% or greater) from expanded polytetrafluoroethylene (ePTFE). Using ePTFE may provide a thin, durable, impermeable material to limit nutrient contact from lined surfaces of the gastric wall. In some examples, the membrane 30 may include elastomer imbibing or folded structure to allow the membrane 30 to be compliant to remain in contact with the internal surface of the gastric wall during peristalsis and other movement of a patient.

In some embodiments, the membrane 30 comprises a fluoropolymer, such as an expanded polytetrafluoroethylene (ePTFE) polymer, or polyvinylidene fluoride (PVDF). In some embodiments, the membrane 30 comprises a polyester, a silicone, a urethane, another biocompatible polymer, polyethylene terephthalate (e.g., Dacron®), copolymers, or combinations thereof.

In some embodiments, the membrane 30 (or portions thereof) is modified by one or more chemical or physical processes that enhance one or more properties of the material. For example, in some embodiments, a hydrophilic coating is applied to the membrane 30 to improve the wettability and echo translucency of the material. In some embodiments, the membrane 30, or portions thereof, is modified with chemical moieties that facilitate one or more of cell attachment, cell migration, cell proliferation, and resistance to or promotion of thrombosis. In some embodiments, the membrane 30, or portions thereof, is modified to resist biofouling. In some embodiments, the membrane 30, or portions thereof, is modified with one or more covalently attached drug substances (e.g., heparin, antibiotics, and the like) or impregnated with the one or more drug substances.

The drug substances can be released in situ to promote healing, reduce tissue inflammation, reduce or inhibit infections, and to promote various other therapeutic treatments and outcomes. In some embodiments, the drug substance is a corticosteroid, a human growth factor, an anti-mitotic agent, an antithrombotic agent, a stem cell material, or dexamethasone sodium phosphate, to name some embodiments. In some embodiments, a pharmacological agent is delivered separately from the membrane 30 to the target site to promote tissue healing or tissue growth.

Coatings and treatments may be applied to the membrane 30 before or after the membrane 30 is joined or disposed on the framework of the stomach lining patch 10. Additionally, one or both sides of the membrane 30, or portions thereof, may be coated. In some embodiments, certain coatings and/or treatments are applied to the membrane 30($s$) located on some portions of the stomach lining patch 10, and other coatings and/or treatments are applied to the material(s) located on other portions of the stomach lining patch 10. In some embodiments, a combination of multiple coatings and/or treatments is applied to the membrane 30, or portions thereof. In some embodiments, certain portions of the membrane 30 are left uncoated and/or untreated. In some embodiments, the stomach lining patch 10 is fully or partially coated to facilitate or frustrate a biological reaction, such as, but not limited to, cell attachment, cell migration, cell proliferation, and resistance to or promotion of thrombosis.

In some embodiments, a first portion of the membrane 30 is formed of a first material and a second portion of the membrane 30 is formed of a second material that is different than the first material. In some embodiments, the membrane 30 includes multiple layers of materials, which may be the same or different materials. In some embodiments, portions of the membrane 30 have one or more radiopaque markers attached thereto to enhance in vivo radiographic visualization of the stomach lining patch 10, or one or more echogenic areas to enhance ultrasonic visibility.

In some embodiments, one or more portions of the membrane 30 are attached to the framework of the stomach lining patch 10, such as the collapsible frame 20 and/or a support structure of the anchoring arms 40. The attachment can be accomplished by a variety of techniques such as, but not limited to, stitching the membrane 30 to the framework of the stomach lining patch 10, adhering the membrane 30 to the framework of the stomach lining patch 10, laminating multiple layers of the membrane 30 to encompass portions of the elongate members of the stomach lining patch 10, using clips or barbs, or laminating multiple layers of the membrane 30 together through openings in the framework of the stomach lining patch 10. In some embodiments, the membrane 30 is attached to the framework of the stomach lining patch 10 at a series of discrete locations thereby facilitating the flexibility of the framework. In some embodiments, the membrane 30 is loosely attached to the framework of the stomach lining patch 10. It is to be appreciated that the membrane 30 may be attached to the framework of the stomach lining patch 10 using other techniques or combinations of techniques described herein.

In some embodiments, the framework of the stomach lining patch 10 (or portions thereof) is coated with a bonding agent (e.g., fluorinated ethylene propylene or other suitable adhesive) to facilitate attachment of the membrane 30 to the framework. Such adhesives may be applied to the framework using contact coating, powder coating, dip coating, spray coating, or any other appropriate means.

The membrane 30 can adapt to changes in the length and/or diameter of the collapsible frame 20 in a variety of manners. In a first example, the membrane 30 can be elastic such that the membrane 30 can stretch to accommodate changes in the length and/or diameter of the stomach lining patch 10. In a second example, the membrane 30 can include slackened material in the low-profile delivery configuration that becomes less slackened or totally unslackened when the stomach lining patch 10 is in the expanded configuration. In a third example, the membrane 30 can include folded portions (e.g., pleats) that are folded in the low-profile configuration and less folded or totally unfolded when the stomach lining patch 10 is in the expanded configuration. In other embodiments, an axial adjustment member is free of the membrane 30. In some embodiments, combinations of such techniques, and/or other techniques can be used whereby the membrane 30 can adapt to changes in the length and/or diameter of the collapsible frame 20.

The anchoring arms 40 extend from the collapsible frame 20 adjacent its center 25. The anchoring arms 40 configured to pass through a puncture in a gastric wall and lay flat against an outer surface of the gastric wall when the collapsible frame 20 and the membrane 30 are in an expanded configuration lining the internal surface of the gastric wall, as shown in FIG. 2C. The anchoring arms 40 may be larger than the holes in the stomach to provide a slight outward radial force on the holes to aid in sealing, e.g., via an interference fit due to the elasticity of the tissues.

The anchoring arms 40 lay flat against the external surface of the gastric wall while the collapsible frame 20 lays flat against the internal surface of the gastric wall to provide apposition forces to the gastric wall surfaces. The collapsible frame 20 and/or the anchoring arms 40 may have preset curves configured to generally conform to the gastric wall surfaces. In some examples, the anchoring arms are radially offset relative to the elements of the collapsible frame 20. The anchoring arms 40 may represent a series of petal shaped wire frames surrounding the center 25, although any variety of other configurations of the anchoring arms 40 may serve as suitable alternatives, such as solid petals rather than wire frame petals.

In some examples, the anchoring arms 40 may be formed from a metal material, such as a metal wire. In the same or different examples, the anchoring arms 40 may be formed from a superelastic material, such as a nitinol material. Such examples may allow a collapsed configuration suitable for endoscopic delivery through elastic deformation of the expanded configuration. The anchoring arms 40 may be formed from a substantially similar material to that of the collapsible frame 20, such as part of a cut tube forming the collapsible frame 20. For example, the collapsible frame 20 and the anchoring arms 40 may include a monolithic frame element forming at least a portion of the collapsible frame 20 and the anchoring arms 40. In some examples, the collapsible frame 20 and the anchoring arms 40 may be formed from a single woven wire, such as a nitinol wire. Alternatively, the collapsible frame 20 and the anchoring arms 40 may be formed from a cut tube structure, such as a cut nitinol tube. In further examples, the collapsible frame 20 and the anchoring arms 40 may be formed from more than one element including any combination of wire elements, and/or cut tube elements.

In various examples, the membrane 30 may cover the anchoring arms 40, or may not cover the anchoring arms 40. In some particular examples, the anchoring arms 40 may be covered in a material that resists ingrowth and adhesion. This may allow the stomach lining patch 10 to be removed later without significant trauma to the surrounding tissues of the gastric wall 102.

Suitable materials for the elongate frame elements of the devices provided herein, such as the collapsible frame 20 and the support structure of the anchoring arms 40, include a variety of metallic materials including alloys exhibiting, shape memory, elastic and super-elastic characteristics. Shape memory refers to the ability of a material to revert to an originally memorized shape after plastic deformation by heating above a critical temperature. Elasticity is the ability of a material to deform under load and return or substantially return to its original shape when the load is released. Most metals will deform elastically up to a small amount of strain. Super-elasticity refers to the ability of a material to deform under strain to much larger degree than typical elastic alloys, without having this deformation become permanent. For example, the super-elastic materials included in the frames of some anastomosis device embodiments provided herein are able to withstand a significant amount of bending and flexing and then return or substantially return to the frame's original form without deformation. In some embodiments, suitable elastic materials include various stainless steels which have been physically, chemically, and otherwise treated to produce a high springiness, metal alloys such as cobalt chrome alloys (e.g., ELGILOY™, MP35N, L605), platinum/tungsten alloys. Embodiments of shape memory and super-elastic alloys include the NiTi alloys, ternary shape memory alloys such as NiTiPt, NiTiCo, NiTiCr, or other shape memory alloys such as copper-based shape memory alloys. Additional materials could combine both shape memory and elastic alloys such as a drawn filled tube where the outer layer is constructed of nitinol and the internal core is a radiopaque material such as platinum or tantalum. In such a construct, the outer layer provides the super-elastic properties and the internal core remains elastic due to lower bending stresses.

In some embodiments, the elongate frame elements used to construct the devices provided herein can be treated in various ways to increase the radiopacity of the devices for enhanced radiographic visualization. In some embodiments, the devices are at least partially a drawn-filled type of NiTi containing a different material at the core, such as a material with enhanced radiopacity. In some embodiments, the devices include a radiopaque cladding or plating. In some embodiments, one or more radiopaque markers are attached to the devices. In some embodiments, the elongate frame elements and/or other portions of the devices provided herein are also visible via ultrasound.

FIGS. 2A-2D illustrate endoscopic implantation of the stomach lining patch 10 within a stomach 100 of a patient. The stomach lining patch 10 is introduced to the stomach 100 as part of an assembly 60 in a collapsed configuration within the endoscopic delivery catheter 50. The illustrated portion of the patient's anatomy in FIGS. 2A-2D includes the stomach 100, the esophagus 110, the pylorus 112, and the duodenum 114 of the patient's small intestine. The stomach 100 includes the gastric wall 102, the antrum 104 and the fundus 106.

As shown in FIG. 2A, the stomach lining patch 10 is delivered to the stomach 100 via the endoscopic delivery catheter 50. In some examples, the stomach lining patch 10 is carried into the stomach 100 proximate the distal end 52 of the endoscopic delivery catheter 50. In other examples, the endoscopic delivery catheter 50 may be passed through the esophagus 110 to locate the distal end 52 within the stomach 100 before the stomach lining patch 10 is pushed through a central lumen of the endoscopic delivery catheter 50, for example, by first loading the stomach lining patch 10 in a proximal end (not shown) of the endoscopic delivery catheter 50 before traversing the length of the central lumen of the endoscopic delivery catheter 50. In such examples, the endoscopic delivery catheter 50 maybe used to facilitate the endoscopic delivery of multiple tools and implants to the stomach 100, such as cameras, surgical tools, and multiple stomach lining patches 10.

In one example technique of implanting the stomach lining patch 10 within the stomach 100, a clinician first inserts the endoscopic delivery catheter 50 through the esophagus 110 to locate the distal end 52 of the endoscopic delivery catheter 50 within the stomach 100. The endoscopic delivery catheter 50 provides access to the stomach 100 for imaging equipment and surgical tools. The clinician then inserts a cutting instrument (not shown) through the endoscopic delivery catheter 50 to a location on an internal surface of the gastric wall 102. The clinician forms the puncture 103 in the gastric wall 102.

The clinician may then withdraw the cutting instrument, and deliver the stomach lining patch 10 in a collapsed configuration to the stomach 100 via the endoscopic delivery catheter, by pushing the stomach lining patch 10 through the central lumen of endoscopic delivery catheter with the plunger 53, as shown in FIG. 2A.

As shown in FIG. 2B, the clinician may then locate the distal end 52 of the endoscopic delivery catheter 50 proximate the puncture 103 and direct the ends of the anchoring arms 40, which protrude from the distal end 52 of the endoscopic delivery catheter 50, through the puncture 103. Once the ends of the anchoring arms 40 are extended through the puncture 103, the clinician may partially deploy the stomach lining patch 10 from the distal end 52 of the endoscopic delivery catheter 50. Once deployed, the anchoring arms 40 may reside in the peritoneal space and lay flat against an outer surface of the gastric wall 102 to minimize the profile of the stomach lining patch 10. The portion of the center of the anchoring arms 40 that passes through the gastric wall 102 should be relatively small to limit trauma to the tissue upon deployment and allow the puncture 103 to heal rapidly upon removal of the stomach lining patch 10.

Next, as shown in FIG. 2C, the clinician may deploy the stomach lining patch 10 from the distal end 52 of the endoscopic delivery catheter 50, e.g., by pushing the stomach lining patch 10 through the central lumen of endoscopic delivery catheter with the plunger 53. Once deployed, the stomach lining patch 10 expands from collapsed configuration within the central lumen of the endoscopic delivery catheter 50 to an expanded configuration. In the expanded configuration, the membrane 30 and the collapsible frame 20 line an internal surface of the gastric wall 102. In this expanded configuration, the collapsible frame 20 lays flat against the internal surface of the gastric wall 102 such that the membrane 30 and the collapsible frame 20 limit nutrient contact from lined portions of the internal surface of the gastric wall 102.

Figure 2D:
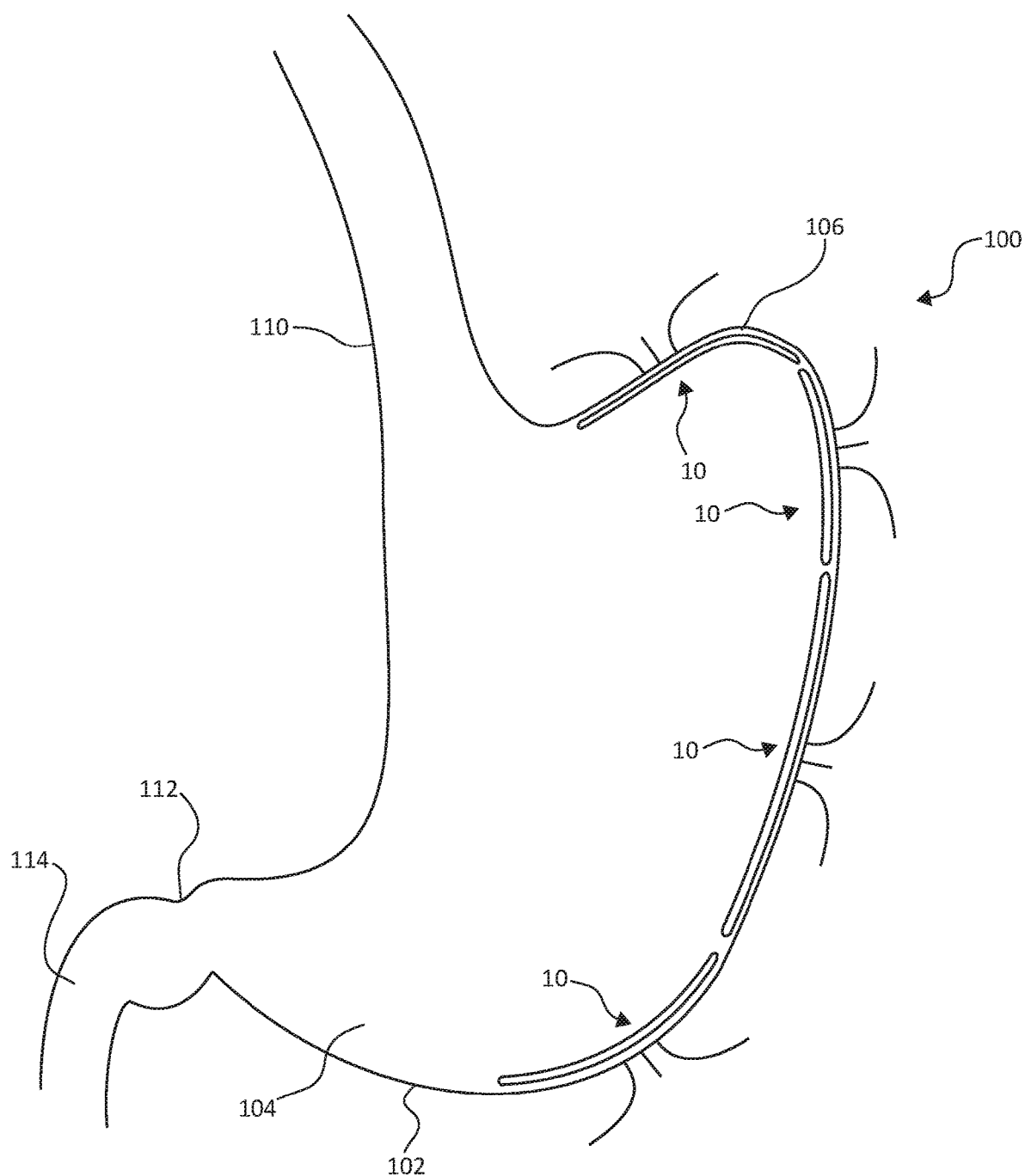

As shown in FIG. 2D, the implantation steps described with respect to FIGS. 2A-2C may be repeated for a number of stomach lining patches 10 to line more of the internal surface of the gastric wall 102 and further limit nutrient contact. In some examples, the stomach lining patches 10 may overlap one another to fully line large areas of the internal surfaces of the gastric wall 102. Such stomach lining patches may effectively exclude the majority of the hormone producing stomach cells, mimicking a vertical sleeve gastrectomy. As shown in FIG. 2D, for example, the stomach lining patches 10 may be located to cover different portions of the gastric wall 102, including portions corresponding to the stomach body, as well as the antrum 104 and the fundus 106. In difference examples, the stomach lining patches 10 may be adapted to conform to various stomach geometries. In other examples, the stomach lining patches 10 may be sufficiently compliant to facilitate lining various stomach geometries without adaptation.

Various modifications may be made to the techniques disclosed herein within the spirit of this disclosure. For example, whereas the stomach lining patch 10 is described as including a set of the anchoring arms 40 that extend through the gastric wall 102 to provide fixation within stomach, other fixation techniques may be applied instead of or in combination with the full gastric wall thickness fixation provided by the anchoring arms 40. For example, in other examples, partial gastric wall thickness fixation techniques may be used, such as any combination of tacks, hooks and/or sutures, such as sutures provided by commercial endoscopic suturing devices. Such examples may utilize modified stomach lining patches 10 with or without the anchoring arms 40.

In various examples, this disclosure covers each of following clauses, as well as the claims provided below, although this disclosure is not limited by the listings of clauses and claims.

Clause 1: A stomach lining patch comprising: a collapsible frame; a membrane covering the collapsible frame, collapsible frame and the membrane providing a collapsed configuration suitable for endoluminal delivery to a stomach of a patient and an expanded configuration suitable for lining an internal surface of a gastric wall of the stomach; and a set of anchoring arms extending from the collapsible frame and being configured to pass through a puncture in the gastric wall and lay flat against an outer surface of the gastric wall when the collapsible frame and the membrane are in an expanded configuration lining the internal surface of the gastric wall.

Clause 2: The stomach lining patch of clause 1, wherein the membrane covers the set of anchoring arms.

Clause 3: The stomach lining patch of clause 1, wherein the collapsible frame and the set of anchoring arms include a monolithic frame element forming at least a portion of the collapsible frame and the set of anchoring arms.

Clause 4: The stomach lining patch of clause 1, wherein the collapsible frame and the set of anchoring arms is formed from a cut tube structure.

Clause 5: The stomach lining patch of clause 1, wherein the collapsible frame, when in the expanded configuration is compliant to remain in contact with the internal surface of the gastric wall during peristalsis.

Clause 6: The stomach lining patch of clause 1, wherein the collapsible frame, when in the expanded configuration, is configured to lay flat against the internal surface of the gastric wall and limit nutrient contact from lined portions of the internal surface of the gastric wall.

Clause 7: The stomach lining patch of clause 1, wherein the membrane includes expanded polytetrafluoroethylene (ePTFE).

Clause 8: The stomach lining patch of clause 1, wherein the collapsible frame is formed from Nitinol.

Clause 9: The stomach lining patch of clause 1, wherein the set of anchoring arms are covered in a material that resists ingrowth and adhesion.

Clause 10: An assembly comprising: an endoscopic delivery catheter; and a stomach lining patch in a collapsed configuration within the endoscopic delivery catheter, the stomach lining patch comprising: a collapsible frame; a membrane covering the collapsible frame, collapsible frame and the membrane providing the collapsed configuration suitable for endoluminal delivery to a stomach of a patient and an expanded configuration suitable for lining an internal surface of a gastric wall of the stomach; and a set of anchoring arms extending from the collapsible frame and being configured to pass through a puncture in the gastric wall and lay flat against an outer surface of the gastric wall when the collapsible frame and the membrane are in an expanded configuration lining the internal surface of the gastric wall.

Clause 11: The assembly of clause 10, wherein the membrane covers the set of anchoring arms.

Clause 12: The assembly of clause 10, wherein the collapsible frame and the set of anchoring arms include a monolithic frame element forming at least a portion of the collapsible frame and the set of anchoring arms.

Clause 13: The assembly of clause 10, wherein the collapsible frame and the set of anchoring arms is formed from a cut tube structure.

Clause 14: The assembly of clause 10, wherein the collapsible frame, when in the expanded configuration is compliant to remain in contact with the internal surface of the gastric wall during peristalsis.

Clause 15: The assembly of clause 10, wherein the collapsible frame, when in the expanded configuration, is configured to lay flat against the internal surface of the gastric wall and limit nutrient contact from lined portions of the internal surface of the gastric wall.

Clause 16: The assembly of clause 10, wherein the membrane includes expanded polytetrafluoroethylene (ePTFE).

Clause 17: The assembly of clause 10, wherein the collapsible frame is formed from Nitinol.

Clause 18: The assembly of clause 10, wherein the set of anchoring arms are covered in a material that resists ingrowth and adhesion.

Clause 19: A method of implanting a stomach lining patch within a stomach of a patient, the method comprising: inserting an endoscopic delivery catheter through an esophagus of the patient to locate a distal end of the endoscopic delivery catheter within the stomach of the patient; forming a puncture in a gastric wall of the stomach; delivering the stomach lining patch in a collapsed configuration to the stomach via the endoscopic delivery catheter, wherein the stomach lining patch includes: a collapsible frame; a membrane covering the collapsible frame, collapsible frame and the membrane providing the collapsed configuration suitable for endoluminal delivery to the stomach of the patient and an expanded configuration suitable for lining an internal surface of a gastric wall of the stomach; and a set of anchoring arms extending from the collapsible frame; inserting the set of anchoring arms through the puncture the gastric wall; deploying the stomach lining patch from the distal end of the endoscopic delivery catheter to expand the stomach lining patch from the collapsed configuration to an expanded configuration, wherein, once deployed, the set of anchoring arms lay flat against an outer surface of the gastric wall and the collapsible frame and the membrane line an internal surface of the gastric wall.

Clause 20: The method of clause 19, wherein the stomach lining patch is a first stomach lining patch, the method further comprising deploying a second stomach lining patch from the distal end of the endoscopic delivery catheter to line more of the internal surface of the gastric wall.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:
1. A stomach lining patch comprising:
a collapsible frame;
a membrane covering the collapsible frame, the collapsible frame and the membrane providing a collapsed configuration suitable for endoluminal delivery to a stomach of a patient and an expanded configuration suitable for lining an internal surface of a gastric wall of the stomach; and
a set of anchoring arms extending from the collapsible frame and being configured to pass through a puncture in the gastric wall and lay flat against an outer surface of the gastric wall when the collapsible frame and the membrane are in an expanded configuration lining the internal surface of the gastric wall, wherein the set of anchoring arms is configured to extend from the collapsible frame adjacent its center.

2. The stomach lining patch of claim 1, wherein the membrane covers the set of anchoring arms.

3. The stomach lining patch of claim 1, wherein the collapsible frame and the set of anchoring arms include a monolithic frame element forming at least a portion of the collapsible frame and the set of anchoring arms.

4. The stomach lining patch of claim 1, wherein the collapsible frame and the set of anchoring arms is formed from a cut tube structure.

5. The stomach lining patch of claim 1, wherein the collapsible frame, when in the expanded configuration is compliant to remain in contact with the internal surface of the gastric wall during peristalsis.

6. The stomach lining patch of claim 1, wherein the collapsible frame, when in the expanded configuration, is configured to lay flat against the internal surface of the gastric wall and limit nutrient contact from lined portions of the internal surface of the gastric wall.

7. The stomach lining patch of claim 1, wherein the membrane includes expanded polytetrafluoroethylene (ePTFE).

8. The stomach lining patch of claim 1, wherein the collapsible frame is formed from Nitinol.

9. The stomach lining patch of claim 1, wherein the set of anchoring arms are covered in a material that resists ingrowth and adhesion.

10. An assembly comprising:
an endoscopic delivery catheter; and
a stomach lining patch including:
a collapsible frame;
a membrane covering the collapsible frame, the collapsible frame and the membrane providing a collapsed configuration suitable for endoluminal delivery to a stomach of a patient and an expanded configuration suitable for lining an internal surface of a gastric wall of the stomach; and
a set of anchoring arms extending from the collapsible frame and being configured to pass through a puncture in the gastric wall and lay flat against an outer surface of the gastric wall when the collapsible frame and the membrane are in an expanded configuration lining the internal surface of the gastric wall, wherein the set of anchoring arms is configured to extend from the collapsible frame adjacent its center;

wherein the stomach lining patch is in a collapsed configuration within the endoscopic delivery catheter.

11. The assembly of claim 10, further comprising a plunger configured to push the stomach lining patch out a distal end of the endoscopic delivery catheter to facilitate deployment of the stomach lining patch within a patient.

12. A method of implanting a stomach lining patch within the stomach of a patient, the method comprising:
- inserting an endoscopic delivery catheter through an esophagus of the patient to locate a distal end of the endoscopic delivery catheter within a stomach of the patient;
- forming a puncture in a gastric wall of the stomach;
- delivering a stomach lining patch in a collapsed configuration to the stomach via the endoscopic delivery catheter, the stomach lining patch including a collapsible frame, a membrane covering the collapsible frame, the collapsible frame and the membrane providing a collapsed configuration suitable for endoluminal delivery to a stomach of a patient and an expanded configuration suitable for lining an internal surface of a gastric wall of the stomach, and a set of anchoring arms extending from the collapsible frame adjacent its center;
- inserting the set of anchoring arms through the puncture the gastric wall;
- deploying the stomach lining patch from the distal end of the endoscopic delivery catheter to expand the stomach lining patch from the collapsed configuration to an expanded configuration,
- wherein, once deployed, the set of anchoring arms lay flat against an outer surface of the gastric wall and the collapsible frame and the membrane line an internal surface of the gastric wall.

13. The method of claim 12, wherein the stomach lining patch is a first stomach lining patch, the method further comprising deploying a second stomach lining patch from the distal end of the endoscopic delivery catheter to line more of the internal surface of the gastric wall.

* * * * *